United States Patent
Iyer et al.

(12) 
(10) Patent No.: US 6,514,402 B2
(45) Date of Patent: Feb. 4, 2003

(54) SENSOR AND METHOD FOR DETECTING AN AIR BORNE OR EXOGENOUSLY INTRODUCED ANALYTE

(75) Inventors: Narayan V. Iyer, Horseheads, NY (US); William J. Lacey, North Andover, MA (US); David M. Root, Westford, MA (US)

(73) Assignee: Corning Incorporated, Corning, NY (US)

( * ) Notice: Subject to any disclaimer, the term of this patent is extended or adjusted under 35 U.S.C. 154(b) by 138 days.

(21) Appl. No.: 09/731,423

(22) Filed: Dec. 6, 2000

(65) Prior Publication Data

US 2001/0040103 A1 Nov. 15, 2001

Related U.S. Application Data

(60) Provisional application No. 60/169,471, filed on Dec. 7, 1999.

(51) Int. Cl.⁷ .................. G01N 27/31; G01N 27/327; G01N 27/333; G01N 27/40
(52) U.S. Cl. .................. 205/793; 205/789; 205/778; 204/416; 204/431; 204/403.06
(58) Field of Search .................. 204/279, 409, 204/403.01, 403.03, 403.06, 403.08, 403.1, 415, 416, 431, 418, 419; 205/775, 777.5, 778, 793, 789

(56) References Cited

FOREIGN PATENT DOCUMENTS

| EP | 0911632 A1 | * 4/1999 |
|---|---|---|
| WO | WO 00/25121 | 5/2000 |

\* cited by examiner

*Primary Examiner*—Jill Warden
*Assistant Examiner*—Alexander Noguerola
(74) *Attorney, Agent, or Firm*—William J. Tucker; Thomas R. Beall

(57) ABSTRACT

The present invention includes a method and sensor that is easy to assemble and can operate to effectively detect an air borne or exogenously introduced analyte. In one embodiment, the assembled sensor includes a top cap capable of receiving a first electrolyte and a bottom cap capable of receiving a second electrolyte. The assembled sensor also includes a flexible boot that holds together the top cap, the bottom cap and a membrane. The membrane is located between the first electrolyte and the second electrolyte and enables an electrical device to detect an analyte (e.g., hazardous chemical) which originally entered the sensor through a passage in the top cap and interacted with the membrane.

24 Claims, 11 Drawing Sheets

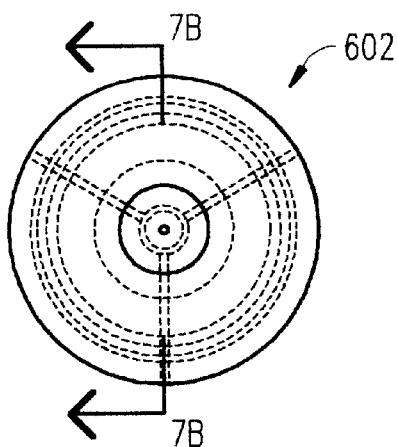
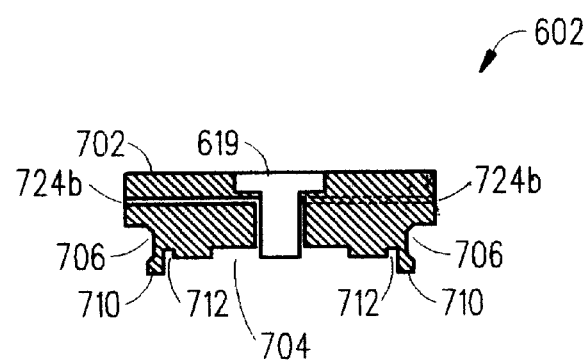
FIG. 7A
FIG. 7B
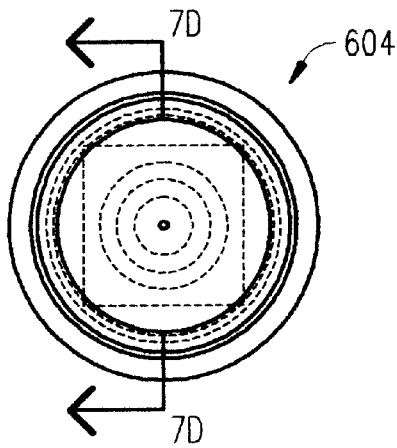
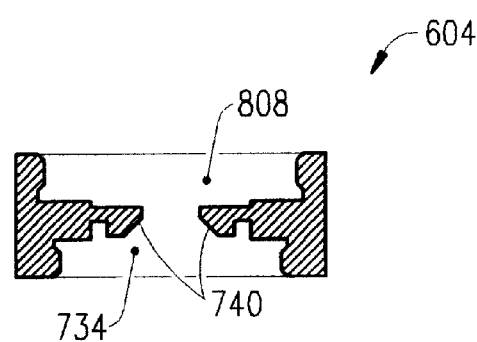
FIG. 7C
FIG. 7D
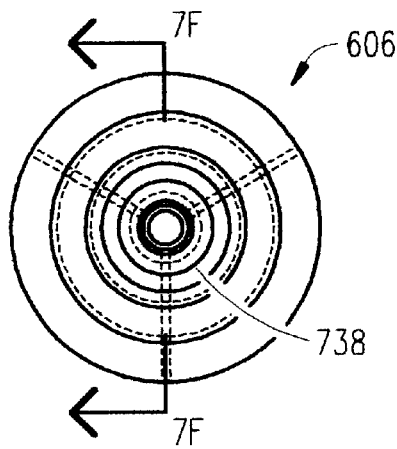
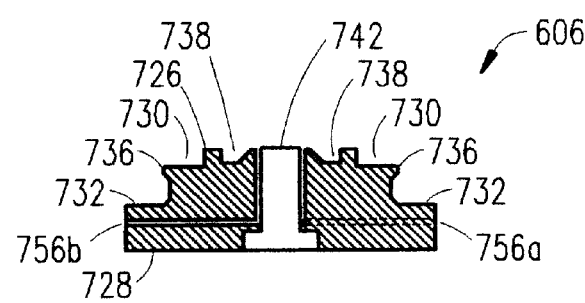
FIG. 7E
FIG. 7F

SENSOR AND METHOD FOR DETECTING AN AIR BORNE OR EXOGENOUSLY INTRODUCED ANALYTE

CLAIMING BENEFIT OF PRIOR FILED PROVISIONAL APPLICATION

This application claims the benefit of U.S. Provisional Application Ser. No. 60/169,471 filed on Dec. 7, 1999 and entitled "Biosensor" which is incorporated by reference herein.

BACKGROUND OF THE INVENTION

1. Field of the Invention

The present invention relates in general to an electrical/biological interface sensor and, in particular, to a sensor and method capable of detecting an air borne or exogenously introduced analyte including, for example, a hazardous chemical.

2. Description of Related Art

Manufacturers of electrical/biological interface sensors have been trying to design such sensors that are both reliable and easy to assemble. An electrical/biological interface sensor is basically a sensor incorporating a biosensor that can transform a biological process into an electrical output when it detects a specific analyte (e.g., hazardous chemical). Examples of traditional electrical/biological interface sensors are briefly discussed below and described in PCT Patent Application No. WO 00/25121 which is hereby incorporated by reference herein.

Referring to FIGS. 1A and 1B (PRIOR ART), there are respectively illustrated a side view and a top view of a traditional sensor 100 described in the aforementioned PCT Patent Application No. WO 00/25121. This traditional sensor 100 is fabricated as a chip and has an electrically insulating barrier defined by a silicone substrate 102 and a thin film insulating layer 104 (e.g., silicone nitride) positioned in electrical communication with an electrical circuit 118, 120 and 122. The electrical circuit 118, 120 and 122 is constructed and arranged to detect changes in the electrical characteristic of an ion channel(s) in a hole 110 covered by a lipid bilayer of the insulating layer 104 which is positioned between two electrolytes 106 and 108.

The two electrolyte containers 112 and 114 are constructed to contain electrolytes 106 and 108, respectively, and to position the electrolytes 106 and 108 in contact with different sides of the insulating layer 104. Container 112 includes a passageway 116 that allows exposure of electrolyte 106 to an analyte. In some cases, the containers 112 and 114 can be removed from and reattached to the electrically insulating barrier 102 and 104 using an adhesive, snap-fit, auxiliary fasteners or the like.

Electrical circuitry 118, 120 and 122 is provided to electrically contact the electrolytes 106 and 108 in containers 112 and 114. As illustrated, a positive bias electrode 118 is partially immersed in the electrolyte 106 and a negative bias electrode 120 is partially immersed in the electrolyte 108. FIG. 1A depicts electrode 120 as being positioned adjacent to one side of insulating layer 104, and electrode 118 is shown as being positioned against the silicon substrate 102 which in turn is positioned against the insulating layer 104. The electrodes 118 and 120 can be connected to an integrated circuit amplifier and bias generator 122 that indicates the presence of an analyte in response to a change in the electrical characteristic of the ion channel(s).

Referring to FIGS. 2A and 2B (PRIOR ART), there are respectively illustrated a disassembled side view and an assembled side view of another traditional sensor 200 described in the aforementioned PCT Patent Application No. WO 00/25121. This traditional sensor 200 includes a barrier 202 having a top side 204 and a bottom side 206 as oriented in the illustrations. The barrier 202 is based upon an annular silicon ring 208 that tapers, at its center, to a relatively large hole. A silicon nitride thin film layer is provided on the bottom side of the silicon ring 208 which includes a hole 210 at its center, concentric with the hole in the center of the silicon ring 208, but much smaller, on the order of 1 micron or less. The silicon nitride thin film layer extends centrally into the hole in the silicon ring 208 and defines part of the electrically insulating barrier. Although, not shown, within hole 210 is a lipid bilayer membrane including an ion channel(s). An electrically insulating layer 212 covers the top side 204 of the silicon ring 208 and extends centrally beyond the silicon ring 208 into the hole within the silicon ring 208 and onto the silicon nitride thin film layer but does not extend to hole 210. Thus, the silicon ring 208, the silicon nitride thin film layer and the electrically insulating layer 212 define the barrier 202.

The tapering portion within the center of the silicon ring 208 is suitable for receiving an electrolyte solution 214. Below the bottom side 206 of the barrier 202 is provided a bottom component 216 which includes a center receptacle 218 positioned for alignment with the hole 210. The receptacle 218 contains an electrode 220 (e.g., silver) and is suitable for receiving a second electrolyte solution 222.

The traditional sensor 200 also includes a top portion 224 having a second electrode 226 (e.g., silver) positioned in or near the center thereof. The bottom portion 216 and the top portion 224 are constructed of an electrically insulating material and designed to snap-fit together, sandwiching therebetween the middle portion including the barrier 202. Seals, such as Sylgard® seals 228 can be provided to mate with portions of the bottom portion 216 and the top portion 224 to create isolated chambers containing the electrolytes 214 and 222 immediately above and below the hole 210.

When the traditional sensor 200 is assembled, the electrolytes 214 and 222 are brought into contact with opposite sides of the hole 210, thus in contact with opposite sides of the ion channel(s) (not shown) within the hole 210. Electrical circuitry (not shown) connects electrodes 220 and 226 and indicates the presence of the analyte in response to a change in the electrical characteristic of the ion channel(s). In other words, when the traditional sensor 200 is exposed to air containing the analyte which passed through passages 230 and diffused through electrolyte 214 and then binded to a pore(s) of the ion channel(s) within hole 210 its presence can be sensed by the electrical circuitry.

Referring to FIGS. 3A and 3B (PRIOR ART), there are respectively illustrated a sectional side view and top view of yet another traditional sensor 300 described in the aforementioned PCT Patent Application No. WO 00/25121. This traditional sensor 300 includes a barrier 302 separating electrolytes 304 and 306 within bottom and top containers 308 and 310, respectively, defined by the connection of bottom component 312 and top component 314, respectively, to barrier 302. As illustrated, the bottom component 312 defines, itself, an electrode addressed by an electrical lead 316, and top component 314 defines, itself, an electrode addressed by an electrical lead 318. Electrolyte solution 304 completely fills the bottom container 308, but electrolyte solution 306 only partially fills the top container 310, the remainder of which is filled with air. This partially assists in compensating for expansion and contraction of the electrolyte solution 306. Electrical leads 316 and 318 can connect to electrical circuitry (not shown) that is similar to the electrical circuitry described above with respect to traditional sensors 100 and 200.

The barrier 302 includes a central portion 320 that is electrically insulating and flexible enough to adjust for thermal expansion and contraction of the electrolyte solution 304 in the bottom container 308 to the extent that electrolyte solution 304 can completely fill the bottom container 308 without void space. The top component 314 includes a central passageway 322 used to introduce the electrolyte solution 306 into the top container 310 such that the electrolyte solution 306 is in contact with a thin film 324. The top component 314 also includes peripheral passages 326 that allow introduction of analyte-containing fluid (e.g. air) into the top container 310 for diffusion through the electrolyte solution 306 into contact with a pore(s) mounted within the thin film 324. The thin film 324 includes a nanoscale hole covered by a lipid bilayer having an ion channel(s) which defines the pore(s).

Unfortunately, the traditional sensors 100, 200 and 300 are not real working models but instead are conceptual models or prototype models used only for experimentation and research. Accordingly, there is a need for a sensor that is easy to assemble and can operate effectively to detect an air borne or exogenously introduced analyte. This need and other needs are satisfied by the sensor and method of the present invention.

BRIEF DESCRIPTION OF THE INVENTION

The present invention includes a method and sensor that is easy to assemble and can operate to effectively detect an air borne or exogenously introduced analyte. In one embodiment, the assembled sensor includes a top cap capable of receiving a first electrolyte and a bottom cap capable of receiving a second electrolyte. The assembled sensor also includes a flexible boot that holds together the top cap, the bottom cap and a biosensor. The biosensor is operational when it is located between the first electrolyte and the second electrolyte and enables an electrical device to detect an analyte (e.g., hazardous chemical) that enters the sensor through a passage in the top cap. In particular, the electrical device can apply a voltage to the first electrolyte, the biosensor and the second electrolyte, and then detect the presence of an analyte interacting with the bibsensor by detecting a change in the electrical characteristic of the biosensor caused by the presence of the analyte. Several different configurations and embodiments of the sensor all of which are easy to assemble and all of which can operate effectively to detect an analyte are described below.

BRIEF DESCRIPTION OF THE DRAWINGS

A more complete understanding of the present invention may be had by reference to the following detailed description when taken in conjunction with the accompanying drawings wherein:

FIGS. 7A–7F respectively illustrate a top view and a sectional side view of a top cap, a flexible boot and a bottom cap of the sensor shown in FIGS. 6A and 6B;

DETAILED DESCRIPTION OF THE DRAWINGS

Referring to FIGS. 4–11, there are disclosed four embodiments of a sensor 400, 600, 900 and 1000, and a preferred method 1100 in accordance with the present invention. Basically, the assembled sensor includes a top cap capable of receiving a first electrolyte and a bottom cap capable of receiving a second electrolyte. The assembled sensor also includes a flexible boot that holds together the top cap, the bottom cap and a biosensor. The biosensor is operational when it is located between the first electrolyte and the second electrolyte and enables an electrical device to detect an analyte (e.g., hazardous chemical) that enters the sensor through a passage in the top cap. In particular, the electrical device can apply a voltage to the first electrolyte, the biosensor and the second electrolyte, and then detect the presence of an analyte interacting with the biosensor by detecting a change in the electrical characteristic of the biosensor caused by the presence of the analyte. Several different configurations and embodiments of the sensor all of which are easy to assemble and all of which can operate effectively to detect an analyte are described below.

Figure 1A:
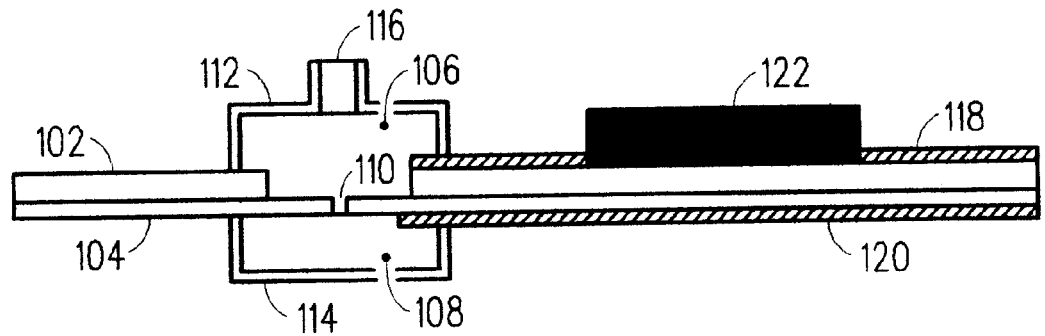
FIGS. 1A and 1B (PRIOR ART) respectively illustrate a side view and a top view of a traditional sensor.
Figure 1B:
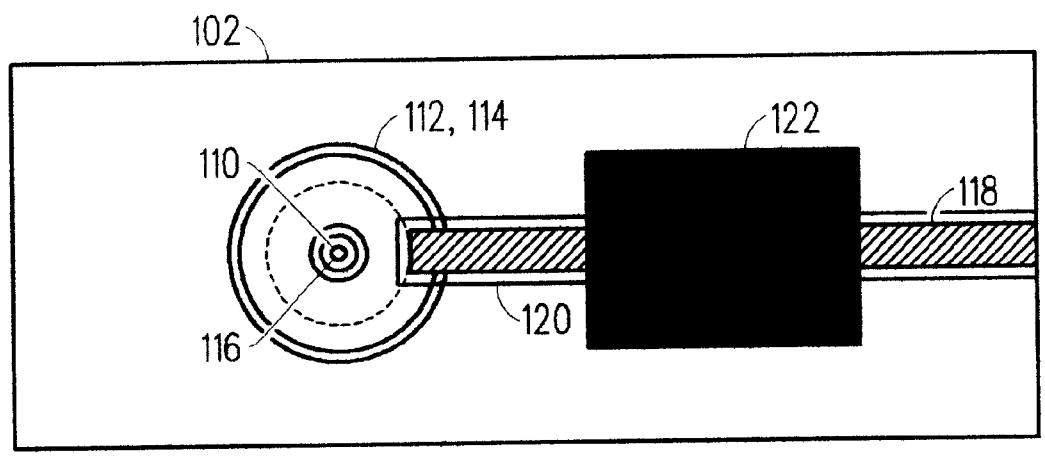
Figure 2A:
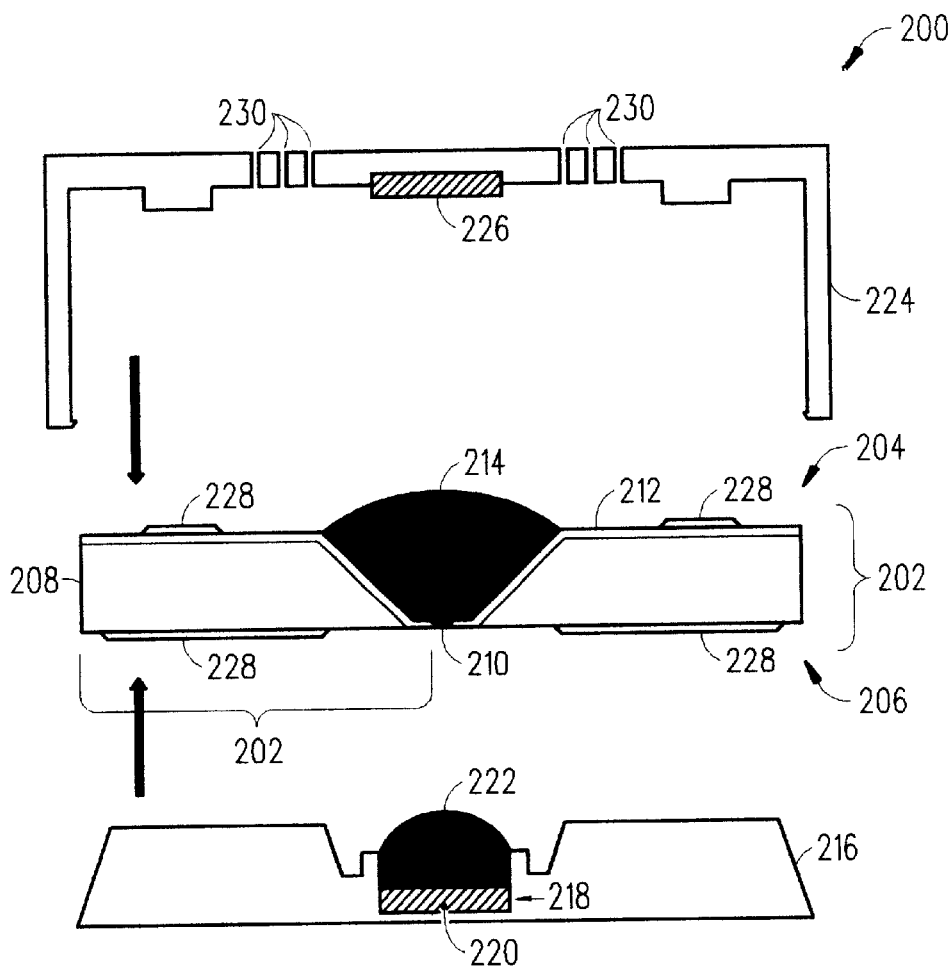
FIGS. 2A and 2B (PRIOR ART) respectively illustrate a disassembled side view and an assembled side view of another traditional sensor.
Figure 2B:
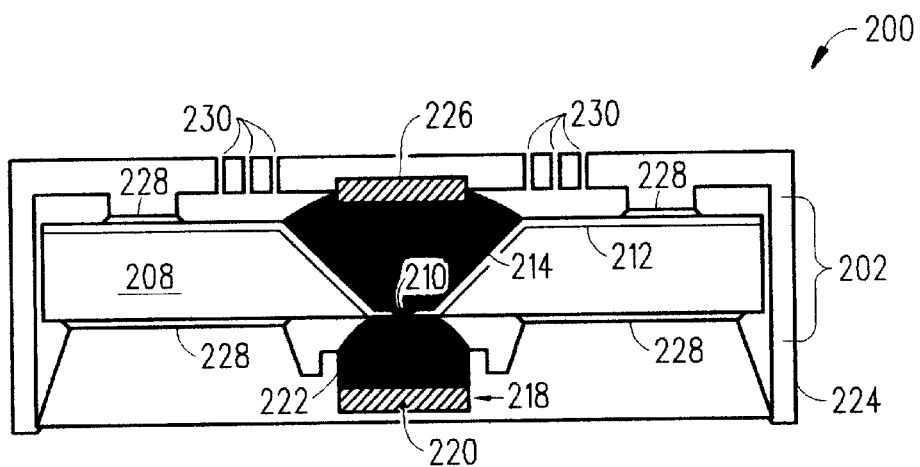
Figure 3A:
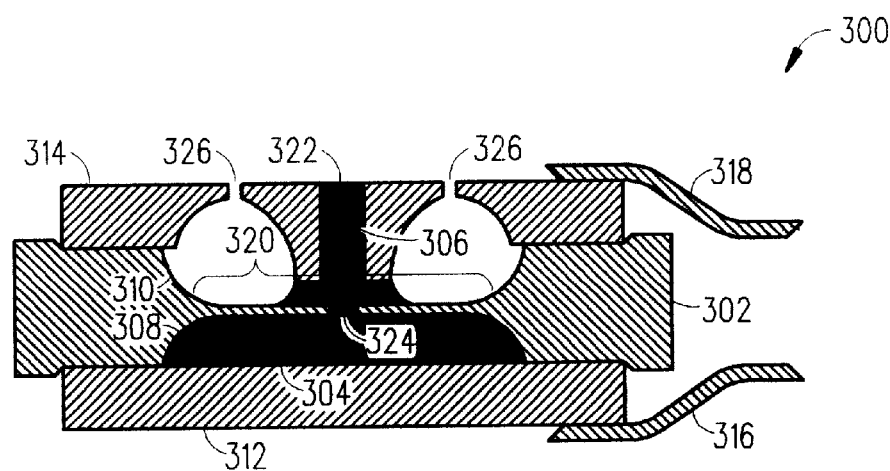
FIGS. 3A and 3B (PRIOR ART) respectively illustrate a sectional side view and a top view of yet another traditional sensor.
Figure 3B:
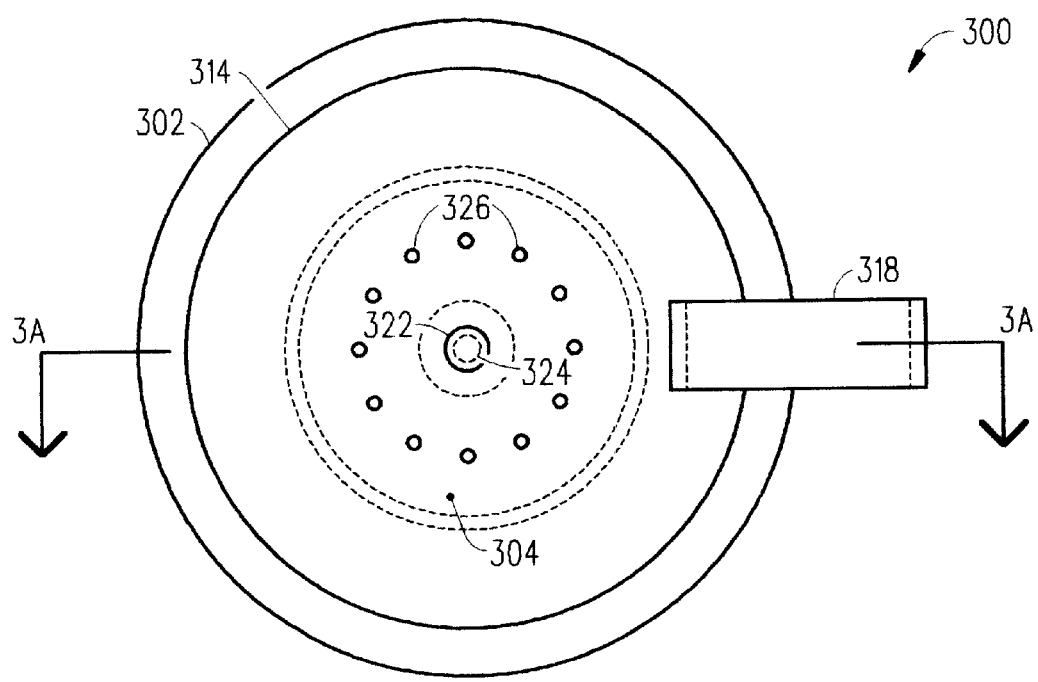
Figure 4A:
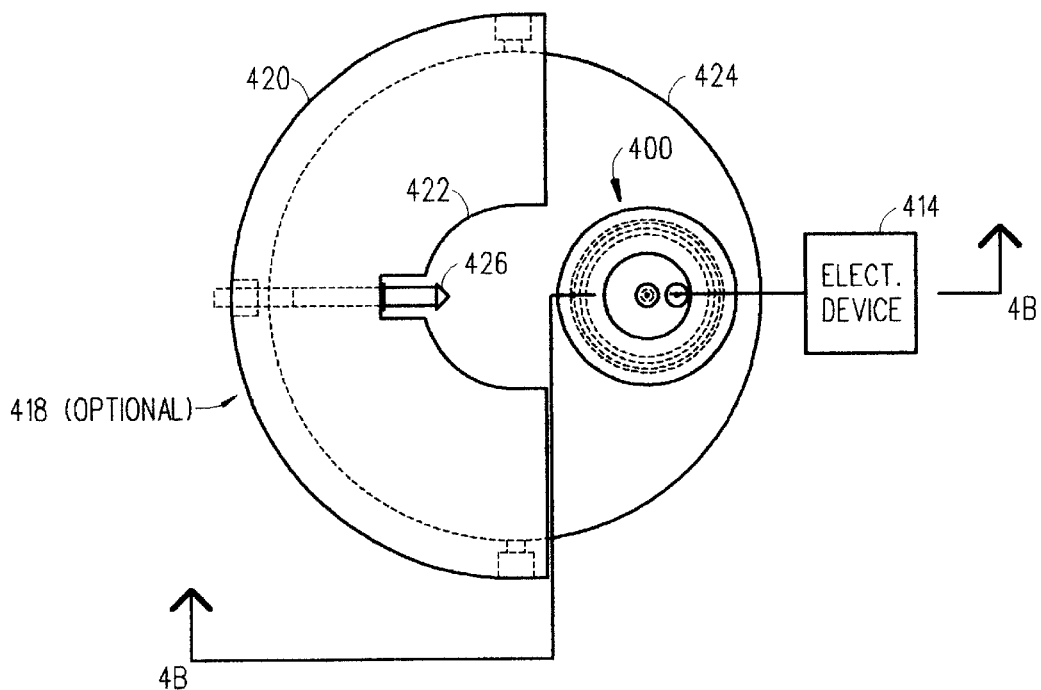
FIGS. 4A and 4B respectively illustrate an assembled top view and an assembled sectional side view of a first embodiment of a sensor in accordance with the present invention.
Figure 4B:
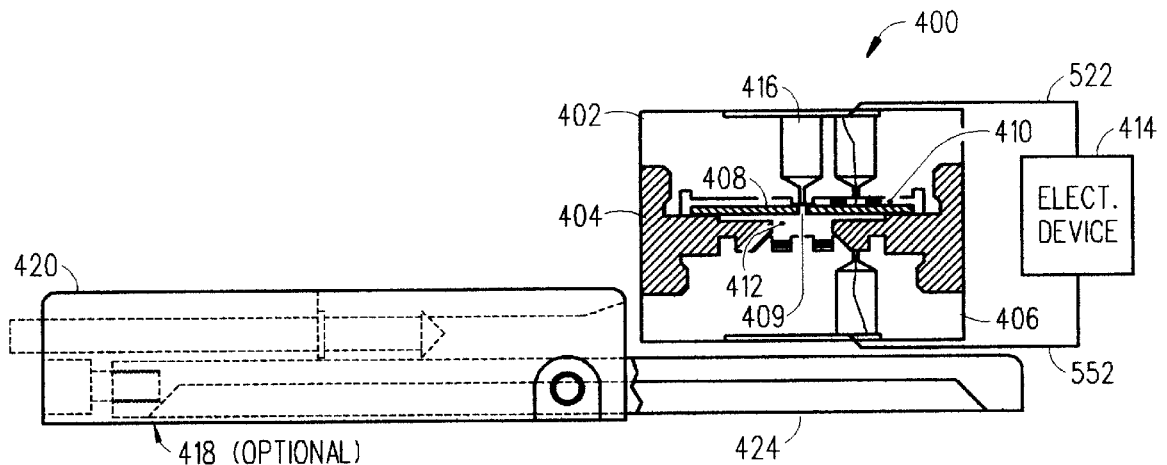

Referring to FIGS. 4A and 4B, there are respectively illustrated an assembled top view and an assembled sectional side view of a first embodiment of a sensor 400. In these illustrations, the sensor 400 includes a top cap 402, a flexible boot 404 and a bottom cap 406. The flexible boot 404 is capable of holding the top cap 402, the bottom cap 406 and a biosensor 408. The biosensor 408 positioned near the bottom side of the top cap 402 is located between a first electrolyte 410 and a second electrolyte 412. The first electrolyte 410 is retained within the top cap 402 and the flexible boot 404. Likewise, the second electrolyte 412 is retained within the bottom cap 406 and the flexible boot 404.

The biosensor 408 is defined by a barrier having at least one hole 409 over which there is supported a membrane having at least one ion channel (e.g., protein). The barrier can be made of insulating materials including, for example, silicone nitride, diamond-like carbon films or other polymeric materials. The biosensor 408 enables an electrical device 414 to detect an analyte (e.g., hazardous chemical) that enters the sensor 400 through a first hole 416 in the top cap 402. In particular, the electrical device 414 can apply a voltage to the first electrolyte 410, the biosensor 408 and the second electrolyte 412, and then detect the presence of an analyte interacting with the biosensor 408 by detecting a change in the electrical characteristic (e.g., current output, oscillation frequency) of the biosensor 408 caused by the presence of the analyte. In other words, the electrical device 414 can sense the presence of the analyte on the biosensor 408 after air containing the analyte is passed through the first hole 416 in the top cap 406, diffused through the first electrolyte 410 and binded to a pore(s) of the ion channel(s) within the biosensor 408. In addition, the electrical device 414 is capable of initiating an alarm when the measured electrical output from at least one ion channel in the biosensor 408 indicates the presence of the analyte. Reference is made to PCT Patent Application No. WO 00/25121 wherein there is disclosed different types of biosensors and their associated electrical characteristics that can be used in the present invention.

In order to assemble the sensor 400, the top cap 402, the biosensor 408 and the bottom cap 406 are placed into the flexible boot 404. The second electrolyte 412 is then inserted through the first hole 416 in the top cap 402 and through the hole 416 in the biosensor 408 onto a top side of the bottom cap 406. Next, the membrane including the ion channel(s) is placed over the hole 416 in the biosensor 408 such that the ion channel(s) is in contact with the second electrolyte 412. The first electrolyte 410 is then inserted through the first hole 416 in the top cap 402 onto the top of the membrane including the ion channel(s) of the biosensor 408. Lastly, the electrical device 414 is connected to the sensor 400.

The assembled sensor 400 can be placed into a base assembly 418 (optional) that can help prevent vibration and electromagnetic noise from adversely affecting the sensor 400. The base assembly 418 includes a top plate 420 having a notch 422 designed to receive all or a portion of the sensor 400. The base assembly 418 also includes a bottom plate 424 on which the sensor 400 can be placed. The sensor 400 can also include a contact rod (not shown) extending into the bottom cap 406 and contacting an electrode 548 (see FIG. 5E). The contact rod is positioned so as to touch a spring contact 426 when the sensor 400 is located within the notch 422. Though not shown the spring contact 426 can be connected to the electrical device 416.

Referring to FIGS. 5A–5F, there are respectively illustrated a top view and a sectional side view of the top cap 402, the flexible boot 404 and the bottom cap 406 of the sensor 400. The top cap 402 has a top side 502 and a bottom side 504 as oriented in FIGS. 5A and 5B. The top cap 402 includes an annular groove 506 located near the bottom side 504 and configured to fit into a top portion 508 of the flexible boot 404 (see FIG. 5D). An edge 510 located near the bottom of the annular groove 506 can also help secure the top cap 402 within the flexible boot 404. A channel 512 may be located near the edge 510 to help prevent leakage of the first electrolyte 410 (see FIG. 4B).

The top cap 402 also includes a first hole 416 extending from the top side 502 to the bottom side 504. The first hole 416 enables the insertion of the first electrolyte 410, the membrane and the second electrolyte 412 into the sensor 400 (see FIG. 4B). In addition, the first hole 416 enables the analyte to enter the assembled sensor 400. The top cap 402 may also include a second hole 514 extending from the top side 502 to the bottom side 504. The second hole 514 can be used to route a wire 516 attached at one end to a conductor shown as a washer 518 which is in contact with the first electrolyte 410 and attached at another end to an electrode 520 located on the top side 502 of the top cap 402. The wire 516, the washer 518 and the electrode 520 are part of an electrical connector 522 that connects to one end of the electrical device 414 (see FIG. 4B). The top cap 402 can be manufactured from an insulating material such as polycarbonate.

Figure 5A:
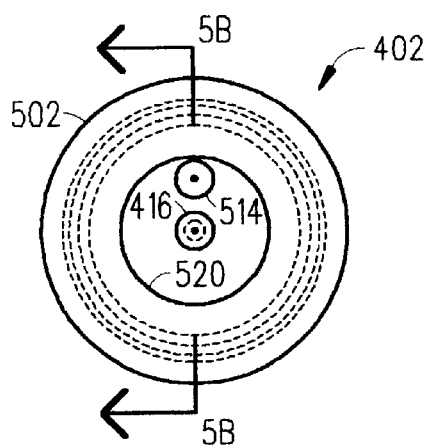
FIGS. 5A–5F respectively illustrate a top view and a sectional side view of a top cap, a flexible boot and a bottom cap of the sensor shown in FIGS. 4A and 4B.
Figure 5B:
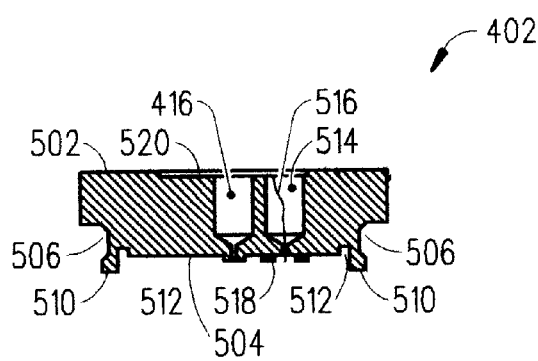
Figure 5C:
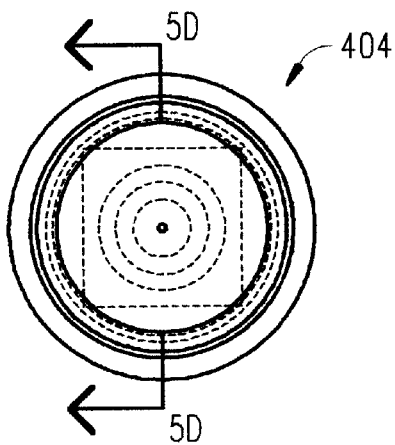
Figure 5D:
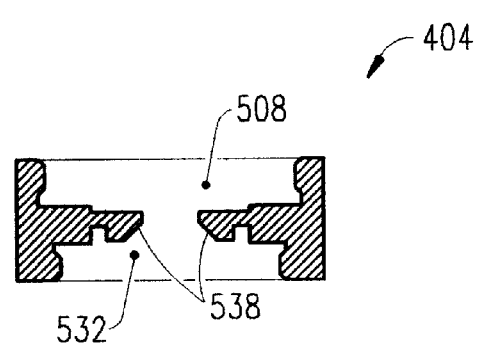
Figure 5E:
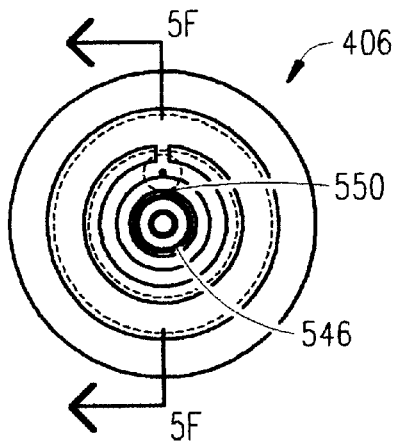
Figure 5F:
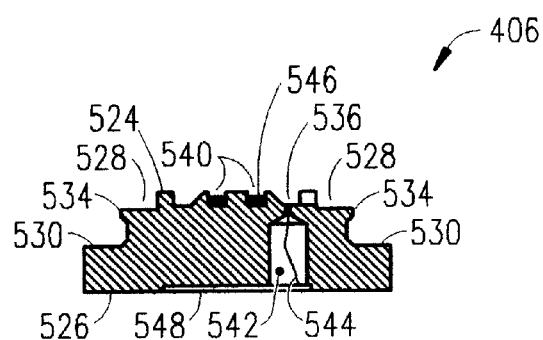

The bottom cap 406 has a top side 524 and a bottom side 526 as oriented in FIGS. 5E and 5F. The bottom cap 406 includes a first annular groove 528 forming part of the top side 524 and also includes a second annular groove 530 located below the first annular groove 528. The first annular groove 528 and the second annular groove 530 are configured to fit into a bottom portion 532 of the flexible boot 404 (see FIG. 5D). An edge 534 positioned between the first annular groove 528 and the second annular groove 530 can also be part of the bottom cap 406 which could help secure the bottom cap 406 within the flexible boot 404.

The bottom cap 406 also includes an outer channel 536 located on the top side 524 and configured to receive part of a middle portion 538 of the flexible boot 404 (see FIG. 5D). An inner channel 540 also formed on the top side 524 of the bottom cap 406 is configured to retain the second electrolyte 412. The bottom cap 406 also includes hole 542 extending from the top side 524 to the bottom side 526. The hole 542 is used to route a wire 544 attached at one end to a conductor shown as a washer 546 in contact with the second electrolyte 412 located in the inner channel 540 and attached at another end to an electrode 548 located on the bottom side 526 of the bottom cap 406 (see FIG. 4B). The wire 544 is shown as passing through a passage 550 between the inner channel 540 and the outer channel 536 (see FIG. 5E). The wire 544, the washer 546 and the electrode 548 are part of an electrical connector 552 that connects to one end of the electrical device 414 (see FIG. 4B). The bottom cap 406 can be manufactured from an insulating material such as polycarbonate. And, the flexible boot 404 can be manufactured from a flexible insulating material such as silicone LIM 6050.

Figure 6A:
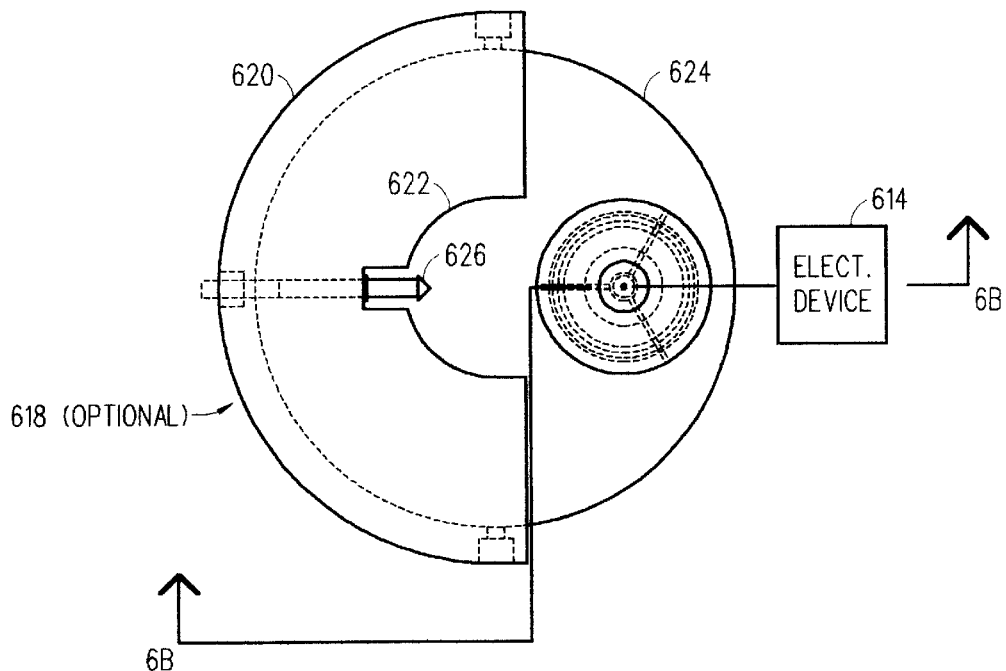
FIGS. 6A and 6B respectively illustrate an assembled top view and an assembled sectional side view of a second embodiment of a sensor in accordance with the present invention.
Figure 6B:
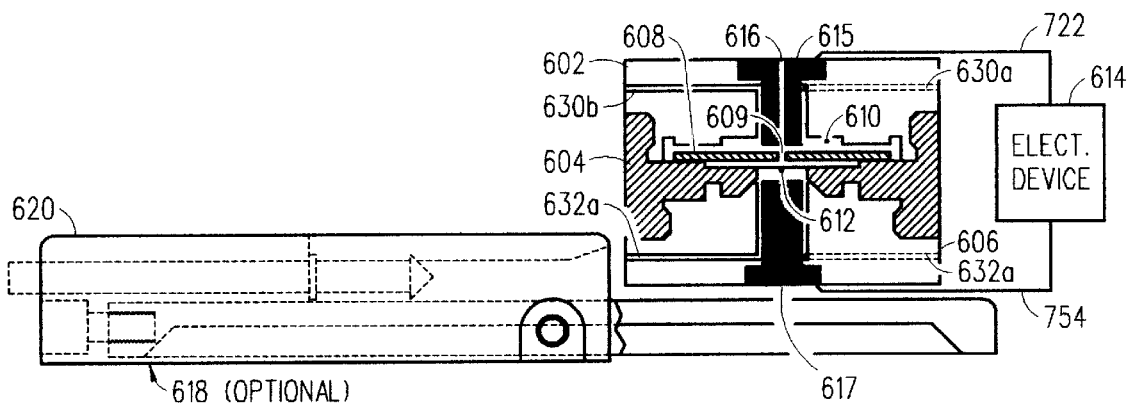

Referring to FIGS. 6A and 6B, there are respectively illustrated an assembled top view and an assembled sectional side view of a second embodiment of a sensor 600. In these illustrations, the sensor 600 includes a top cap 602, a flexible boot 604 and a bottom cap 606. The flexible boot 604 is capable of holding the top cap 602, the bottom cap 606 and a biosensor 608. The biosensor 608 positioned near the bottom side of the top cap 602 is located between a first electrolyte 610 and a second electrolyte 612. The first electrolyte 610 is retained within the top cap 602 and the flexible boot 604. Likewise, the second electrolyte 612 is retained within the bottom cap 606 and the flexible boot 604.

The biosensor 608 is defined by a barrier having at least one hole 609 over which there is supported a membrane having at least one ion channel (e.g., protein). The barrier can be made of insulating materials including, for example, silicone nitride, diamond-like carbon films or other polymeric materials. The biosensor 608 enables an electrical device 614 to detect an analyte (e.g., hazardous chemical) that enters the sensor 600 through a first hole 616 in stud 615 inserted within the top cap 602 (see also FIGS. 8A and 8B for an alternative top cap 602'). In particular, the electrical device 614 can apply a voltage to the first electrolyte 610, the biosensor 608 and the second electrolyte 612, and then detect the presence of an analyte interacting with the biosensor 608 by detecting a change in the electrical characteristic (e.g., current output, oscillation frequency) of the biosensor 608 caused by the presence of the analyte. In other words, the electrical device 614 can sense the presence of the analyte on the biosensor 608 after air containing the analyte is passed through the first hole 616 in the stud 615, diffused through the first electrolyte 610 and binded to a pore(s) of the ion channel(s) within the biosensor 608. In addition, the electrical device 614 is capable of initiating an alarm when the measured electrical output from at least one ion channel in the biosensor 608 indicates the presence of the analyte. Reference is made to PCT Patent Application No. WO 00/25121 wherein there is disclosed different types of biosensors and their associated electrical characteristics that can be used in the present invention.

In order assemble the sensor 600, the top cap 602 (without stud 615), the biosensor 608 and the bottom cap 606 (with stud 617) are placed into the flexible boot 604. The membrane having the ion channel(s) is then placed on the biosensor 608 through hole 616. Next, the stud 615 is inserted into hole 617 the top cap 602 (see FIG. 7B). The first electrolyte 610 is then inserted through tubing 630a extending through the top cap 602 onto at least the membrane of the biosensor 608. As shown in FIG. 6B, the first electrolyte 610 may be located adjacent to the stud 615. In addition, the first electrolyte 610 and air may exit through tubing 630b that also extends through the top cap 602. After insertion of the first electrolyte 610, the external ends of the tubing 630a and 630b may be pinched or clamped to prevent leakage of the first electrolyte 610. Likewise, the second electrolyte 620 is inserted through tubing 632a extending through the bottom cap 606 onto at least the membrane of the biosensor 608. As shown in FIG. 6B, the second electrolyte 612 may be located adjacent to a stud 617 inserted within the bottom cap 606. In addition, the second electrolyte 612 and air may exit through tubing 632b that also extends through the bottom cap 606. After insertion of the second electrolyte 612, the external ends of the tubing 632a and 632b may be pinched or clamped to prevent leakage of the second electrolyte 612. It does not matter in what order the first electrolyte 610 and the second electrolyte 612 are inserted into the sensor 600. Lastly, the electrical device 616 is connected to the sensor 600.

The assembled sensor 600 can be placed into a base assembly 618 (optional) that can help prevent vibration and electromagnetic noise from adversely affecting the sensor 600. The base assembly 618 includes a top plate 620 having a notch 622 designed to receive all or a portion of the sensor 600. The base assembly 618 also includes a bottom plate 624 on which the sensor 600 can be placed. The sensor 600 can also include a contact rod (not shown) extending into the bottom cap 606 and contacting the stud 617. The contact rod is positioned so as to touch a spring contact 626 when the sensor 600 is located within the notch 622. Though not shown the spring contact 626 can be connected to the electrical device 614.

Referring to FIGS. 7A–7F, there are respectively illustrated a top view and a sectional side view of the top cap 602, the flexible boot 604 and the bottom cap 606 of the sensor 600. The top cap 602 has a top side 702 and a bottom side 704 as oriented in FIGS. 7A and 7B. The top cap 602 includes an annular groove 706 located near the bottom side 704 and configured to fit into a top portion 708 of the flexible boot 604 (see FIG. 7D). An edge 710 located near the bottom of the annular groove 706 can also help secure the top cap 402 within the flexible boot 404. A channel 712 may be located near the edge 710 to help prevent leakage of the first electrolyte 610 (see FIG. 6B).

The top cap 602 includes a hole 619 extending from the top side 702 to the bottom side 704. The hole 619 enables the insertion of the stud 615 which forms part of an electrical connector 722 that connects to one end of the electrical device 614 (see FIG. 6B). In addition, the top cap 602 includes two passages 724a and 724b each of which extends from a side of the top cap 602 into the hole 619. Tubings 630a and 630b can be respectively inserted into passages 724a and 724b which are used to insert the first electrolyte 610 into the top cap 602. A hypodermic needle can be used to insert the first electrolyte 610. The top cap 602 can be manufactured from an insulating material such as polycarbonate.

The bottom cap 606 has a top side 726 and a bottom side 728 as oriented in FIGS. 7E and 7F. The bottom cap 606 includes a first annular groove 730 forming part of the top side 726 and also includes a second annular groove 732 located below the first annular groove 730. The first annular groove 730 and the second annular groove 732 are configured to fit into a bottom portion 734 of the flexible boot 604 (see FIGS. 6B and 7D). An edge 736 located between the first annular groove 730 and the second annular groove 732 can also help secure the bottom cap 706 within the flexible boot 704.

The bottom cap 706 also includes an outer channel 738 formed within the top side 726 and configured to receive part of a middle portion 740 of the flexible boot 604 (see FIGS. 6B and 7D). The bottom cap 606 also has hole 742 extending from the top side 726 to the bottom side 728. The hole 742 enables the insertion of the stud 617 which forms part of an electrical connector 754 that connects to one end of the electrical device 614 (see FIG. 6B). In addition, the bottom cap 606 includes two passages 756a and 756b each of which extends from a side of the bottom cap 606 into hole 742. Tubings 632a and 632b can be respectively inserted into passages 756a and 756b and used to insert the second electrolyte 612 in the same manner the first electrolyte 610 is inserted into the top cap 602. The bottom cap 606 can be manufactured from an insulating material such as polycarbonate. And, the flexible boot 604 can be manufactured from a flexible insulating material such as silicone LIM 6050.

Figure 8A:
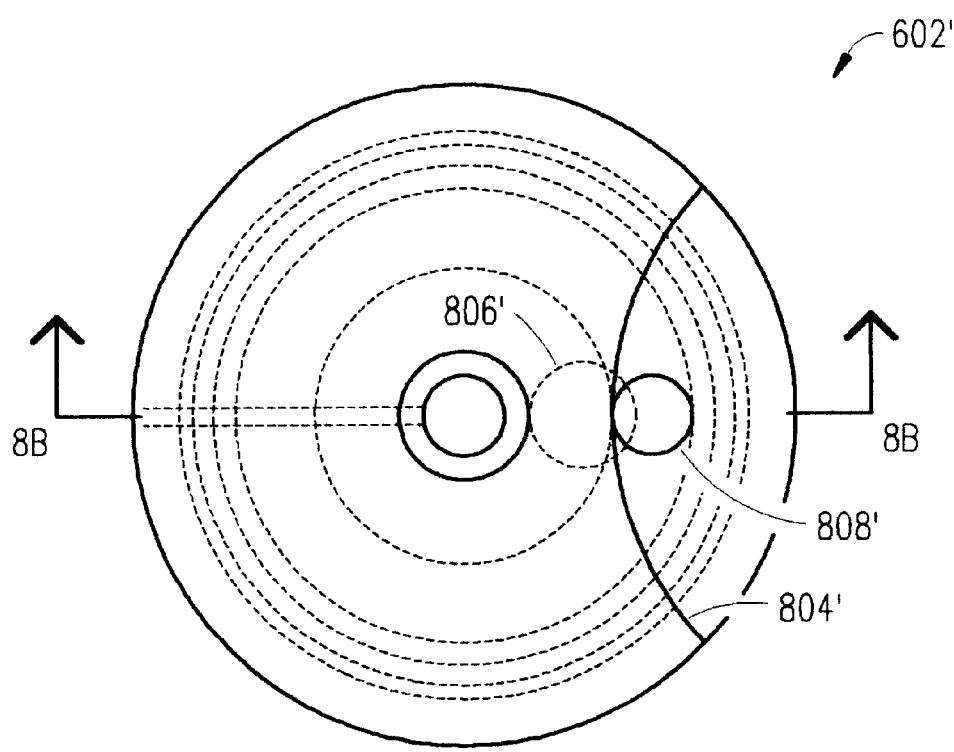
FIGS. 8A–8B respectively illustrate a top view and a sectional side view of an alternative top cap of the sensor shown in FIGS. 6A and 6B.
Figure 8B:
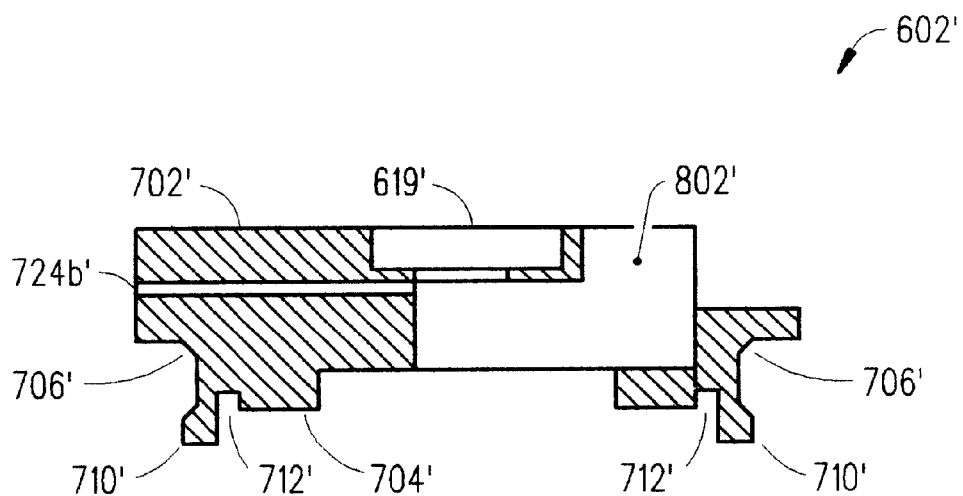

Referring to FIGS. 8A and 8B, there are respectively illustrated a top view and a sectional side view of an alternative top cap 602' of the sensor 600. Basically, the alternative top cap 602' has a configuration that makes it easier for the sensor 600 to receive and analyze an analyte. Similar to the top cap 602, this top cap 602' has a top side 702' and a bottom side 704' as oriented in FIGS. 8A and 8B. The top cap 602' includes an annular groove 706' located near the bottom side 704' and configured to fit into a top portion 708 of the flexible boot 604 (see FIG. 7D). An edge 710' located near the bottom of the annular groove 706' can also help secure the top cap 402 within the flexible boot 404. A channel 712' may be located near the edge 710' to help prevent leakage of the first electrolyte 610 (see FIG. 6B). The top cap 602' also includes a hole 619' extending from the top side 702' to the bottom side 704'. The hole 619' enables the insertion of the stud 615' which forms part of an electrical connector 722 that connects to one end of the electrical device 614 (see FIG. 6B). In addition, the top cap 602' includes at least one passage 724b' (only one passage shown) which extends from a side of the top cap 602' into hole 619'. Tubing 630b' can be inserted into passage 724b.

To make it easier for the sensor 600 to receive and analyze an analyte, the top cap 602' also includes an opening 802' that extends from the top side 702' down to where the first electrolyte 610 is located. As illustrated, the opening 802' can be defined by a notch 804' (shown as a semicircle in FIG. 8A) made into the top side 702' and is also defined by a passage 806' located between hole 617' and passage 808'. The locations of passage 806', hole 617' and passage 808' makes it easier for the analyte to reach the first electrolyte 610'. As before, the top cap 602' can be manufactured from an insulating material such as polycarbonate.

Figure 9:
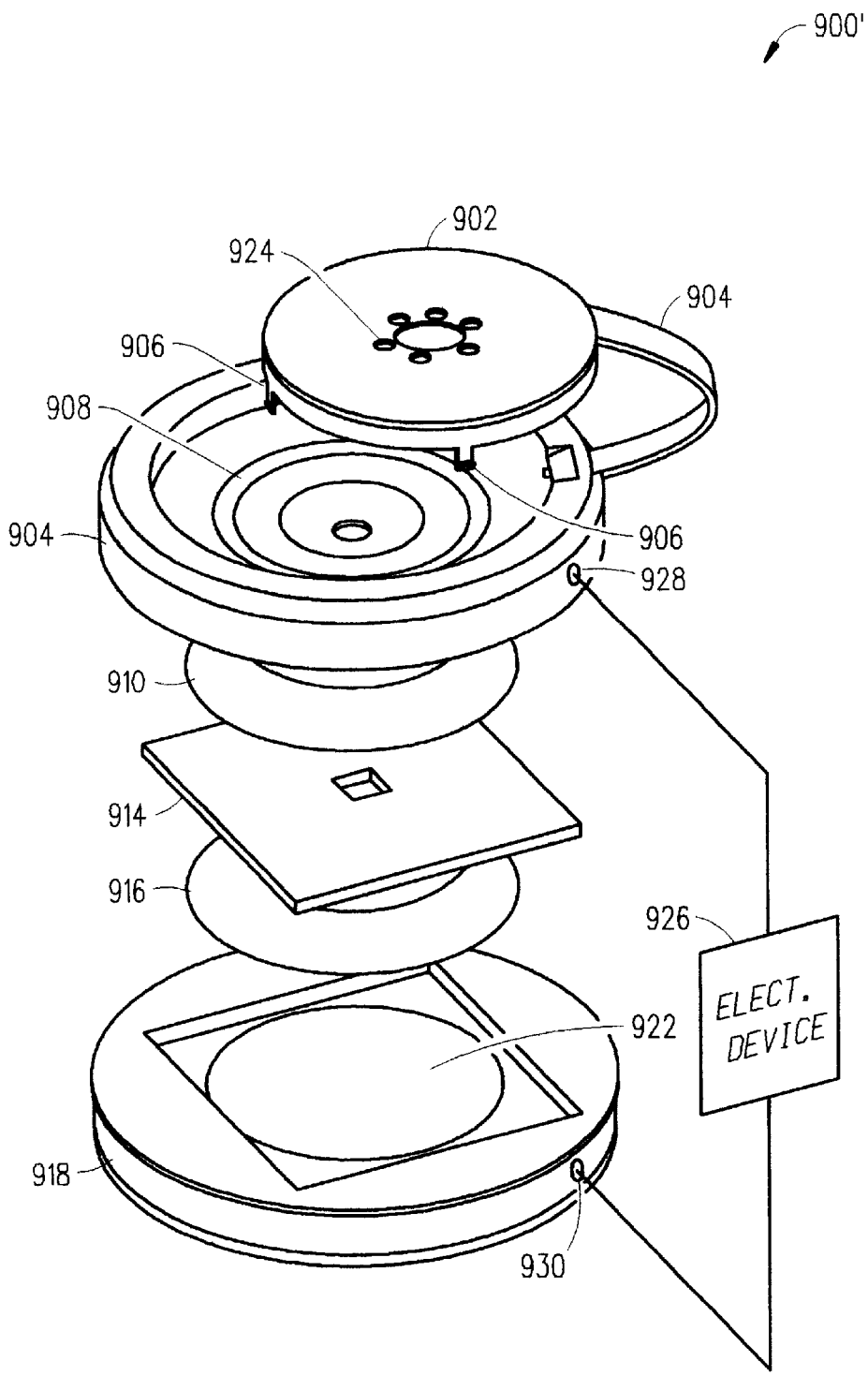
FIG. 9 illustrates a disassembled view of a third embodiment of a sensor in accordance with the present invention.

Referring to FIG. 9, there is illustrated a disassembled view of a third embodiment of a sensor 900. This sensor 900 includes a top cover 902 fixably attached to a center chamber 904 using, for example, a hinge 904 and hooks 906 (as shown) or a snap fit. The center chamber 904 includes a first electrode 908 that can be formed, for example, by printing with a metallic ink or using a plating process. A first O ring 910 is positioned within the center chamber 904 and operates to retain a first electrolyte (not shown). The first electrode 908 is positioned so as to be in electrical communication with the first electrolyte.

The sensor 900 also includes a biosensor 914 located between the first O ring 910 and a second O ring 916. The second O ring 916 is positioned within a lower chamber 918 and operates to retain a second electrolyte (not shown). The lower chamber 918 also includes a second electrode 922 that can be formed, for example, by printing with a metallic ink or using a plating process. The second electrode 922 is positioned so as to be in electrical communication with the second electrolyte. The lower chamber 918 is fixably attached to the center chamber 904 using, for example, a snap fit. The steps to insert the first electrolyte, the second electrolyte, the membrane and the ion channels(s) into sensor 900 are very similar to the steps needed to do the same in assembling sensor 400.

Like the other embodiments, the ion channel(s) (e.g., protein) in the biosensor 914 is positioned between the first electrolyte and the second electrolyte and is used to enable detection of an analyte passing through a passage(s) 924 in the top cover 902. As above, an electrical device 926 can detect the presence of the analyte by detecting a change in the electrical characteristic of the biosensor 914. The electrical circuit can be established, by coupling the electrical device 926 to the first electrode 908 using an electrical hookup 928 and also coupling the electrical device 926 to the second electrode 922 using another electrical hookup 930. In addition, the electrical device 926 is capable of initiating an alarm when the measured electrical output from at least one ion channel in the biosensor 914 indicates the presence of the analyte.

Alternatively, the first O ring 910 and the second O ring 916 of the sensor 900 can be eliminated when the center chamber 918 and the lower chamber 904 each having a form that can respectively hold the first and second electrolytes are molded out of an elastomeric material such as Kraton® or Santoperene®.

Figure 10:
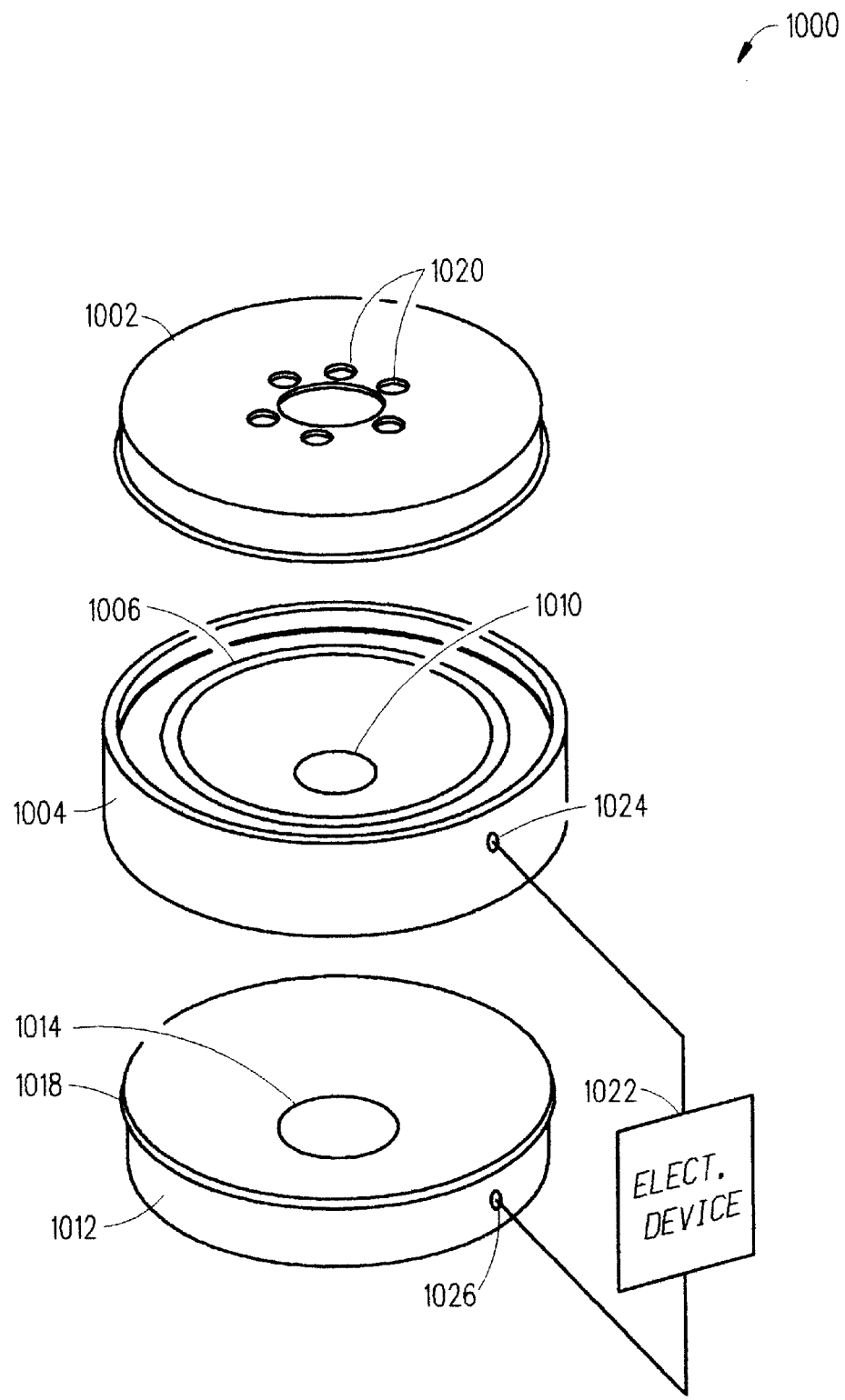
FIG. 10 illustrates a disassembled view of a fourth embodiment of a sensor in accordance with the present invention.

Referring to FIG. 10, there is illustrated a disassembled view of a fourth embodiment of a sensor 1000. This sensor 1000 includes a top cover 1002 fixably attached to a center chamber 1004 using, for example, a snap fit (as shown) or a hinge. The center chamber 1004 includes a first electrode 1006 that can be formed, for example, by printing with a metallic ink or using a plating process. The center chamber 1004 is also configured to retain a first electrolyte (not shown). The first electrode 1006 is positioned so as to be in electrical communication with the first electrolyte. A biosensor 1010 that can be a heat sealed film is attached to the bottom of the center chamber 1004. Then a hole (e.g., 1 micron hole) is ion drilled or laser drilled into the film so that a protein (e.g., ion channel(s)) can be positioned onto the hole.

The sensor 1000 also includes a lower chamber 1012 that can be connected to the center chamber 1004 using, for example, a snap fit. The lower chamber 1012 includes a second electrode 1014 that can be formed, for example, by printing with a metallic ink or using a plating process. Alternatively, the second electrode 1014 can be formed on the bottom of the center chamber 1004. The lower chamber 1012 is also configured to retain a second electrolyte (not shown) in a manner such that the second electrolyte is in electrical communication with the second electrode 1014. A rim 1018 around the edge of the lower chamber 1012 helps contain the second electrolyte. The second electrolyte can be placed in the lower chamber 1012 and then the lower chamber 1012 and the center chamber 1004 can be put together. Thereafter, the protein is placed on the biosensor 1010 and the first electrolyte is placed in the center chamber 1004 and the top cover 1002 attached to the center chamber 1004.

Like the other embodiments, the ion channel(s) (e.g., protein) in the biosensor 1010 is positioned between the first electrolyte and the second electrolyte and is used to enable detection of an analyte passing through a passage(s) 1020 in the top cover 1002. As above, an electrical device 1022 can detect the presence of the analyte by detecting a change in the electrical characteristic of the biosensor 1010. The electrical circuit can be established, by coupling the electrical device 1022 to the first electrode 1006 using an electrical hookup 1024 and also coupling the electrical device 1022 to the second electrode 1014 using another electrical hookup 1026. In addition, the electrical device 1022 is capable of initiating an alarm when the measured electrical output from at least one ion channel in the biosensor 1010 indicates the presence of the analyte.

Figure 11:
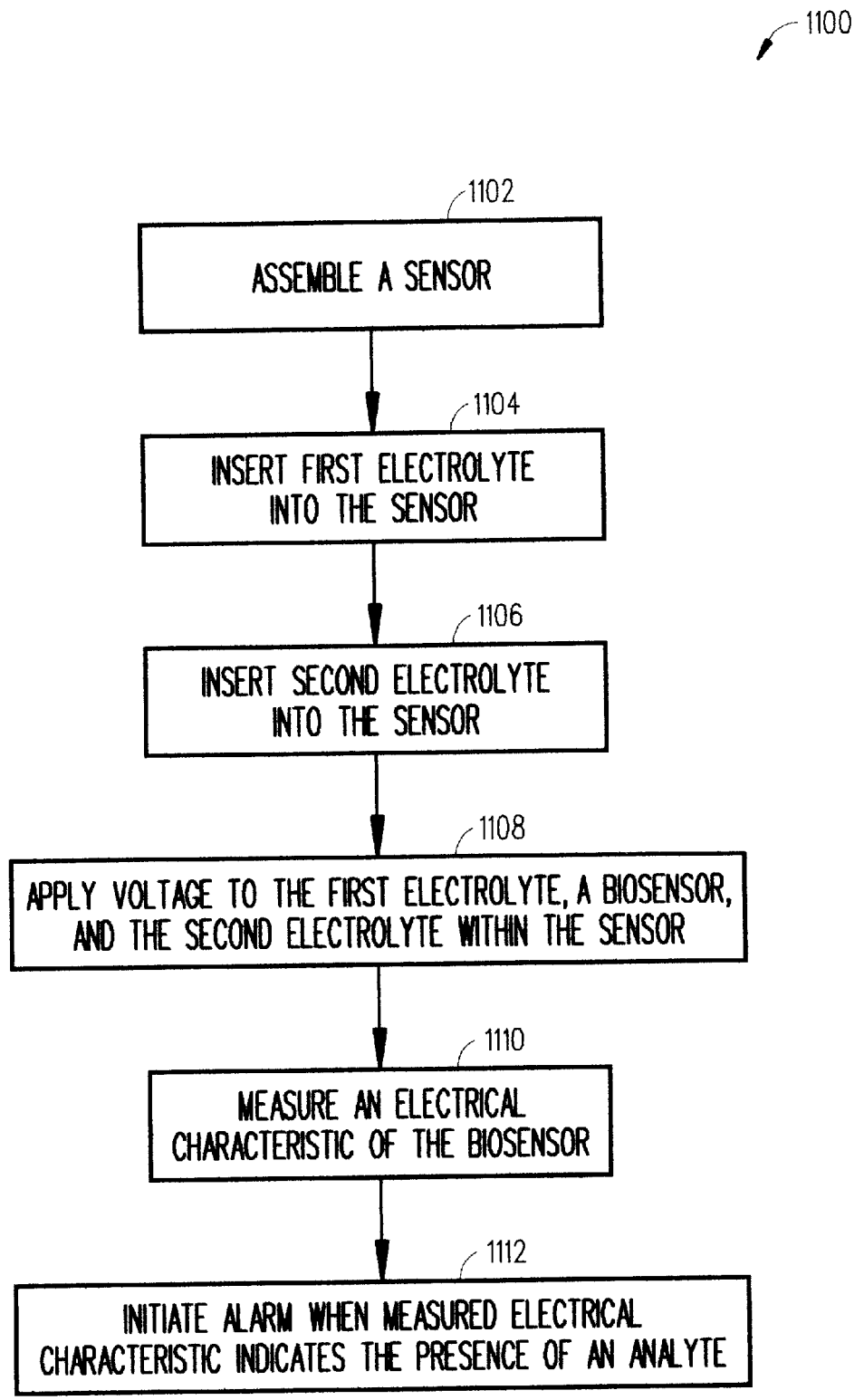
FIG. 11 is a flowchart illustrating the steps of a preferred method of the present invention.

Referring to FIG. 11, there is a flowchart illustrating the steps of a preferred method 1100 for detecting an air borne or exogenously introduced analyte. Beginning at step 1102, a sensor 400, 600, 900 or 1000 is assembled. The different components of sensors 400, 600, 900 and 1000 and how they connect to one another have been described above with respect to FIGS. 4–10.

As an option, the assembled sensor 400, 600, 900 and 1000 can be placed within a base assembly 418 and 618 which can help prevent vibration and electromagnetic noise from adversely affecting the sensor 400, 600, 900 and 1000 (see FIGS. 4 and 6).

At step 1104, a first electrolyte is inserted into the sensor 400, 600, 900 or 1000. For instance, a hypodermic needle can be used to insert the first electrolyte 610 through tubing 630a into the top cap 602 (see FIGS. 6B and 7B).

At step 1106, a second electrolyte is inserted into the sensor 400, 600, 900 or 1000. For instance, a hypodermic needle can be used to insert the second electrolyte 612 through tubing 632a into the bottom cap 606 (see FIGS. 6B and 7F).

At step 1108, an electrical device applies a voltage to the first electrolyte, the biosensor (including the ion channel(s)) and the second electrolyte within the assembled sensor 400, 600, 900 and 1000.

At step 1110, the electrical device measures an electrical output (electrical characteristic) from the biosensor. The measured electrical output (e.g., current output, oscillation frequency) can indicate the presence of the analyte.

The sensor 400, 600, 900 and 1000 can be used to detect the presence of a wide variety of substances including, for example, the presence of a hazardous chemical or the presence of spoiled food. In addition, the sensor 400, 600, 900 and 1000 can be used in a pharmaceutical drug screening application or used to design a manufacturing process. Moreover, the sensor 400, 600, 900 and 1000 can be scaled down to a microtither plate to enable a high throughput-screening mode.

At step 1112, the electrical device initiates an alarm when the measured electrical output from the biosensor indicates the presence of the analyte. For instance, the electrical device can output an signal indicating the presence of an analyte in a variety of ways including, for example, on an X-Y chart, as an alarm light (e.g., LED), or as an alarm sound. Also possible, is that if the sensor 400, 600, 900 and 1000 is dropped from a parachute (for example) and it detects a hazardous substance then an alarm signal can be transmitted to a remote station.

It should be understood that the dimensions of the sensor 400, 600, 900 and 1000 are relatively small. For instance, the sensor 400, 600, 900 and 1000 can be less than 1" high and less than 1" in diameter and easily carried by a person (e.g., soldier).

Although several embodiments of the present invention has been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. A sensor, comprising:
   a top cap capable of receiving a first electrolyte;
   a bottom cap capable of receiving a second electrolyte; and
   a flexible boot capable of holding said top cap, said bottom cap and a membrane located between the first electrolyte and the second electrolyte, wherein said membrane is used to enable detection of an analyte.

2. The sensor of claim 1, further comprising:
   a first tube located within said top cap used to insert the first electrolyte into said top cap; and
   a second tube located within said bottom cap used to insert the second electrolyte into said bottom cap.

3. The sensor of claim 1, further comprising:
   a first electrical connector, associated with said top cap, capable of being in electrical communication with the first electrolyte; and
   a second electrical connector, associated with said bottom cap, capable of being in electrical communication with the second electrolyte.

4. The sensor of claim 3, wherein:
   said first electrical connector includes a wire connecting an electrode to a washer in contact with the first electrolyte; and
   said second electrical connector includes a wire connecting an electrode to a washer in contact with the second electrolyte.

5. The sensor of claim 3, wherein:
   said first electrical connector includes a stud at least partially in contact with the first electrolyte; and
   said second electrical connector includes a stud at least partially in contact with the second electrolyte.

6. The sensor of claim 3, further comprising an electrical device, coupled to the first electrical connector and the second electrical connector, including a voltage source for applying a voltage to the first electrolyte, the membrane and the second electrolyte and a detector for measuring an electrical characteristic of the membrane.

7. The sensor of claim 6, wherein said electrical device is capable of initiating an alarm when the measured electrical characteristic of an at least one ion channel in the membrane indicates the presence of the analyte.

8. The sensor of claim 1, wherein said sensor is positioned within a base assembly which helps prevent vibration and electromagnetic noise from adversely affecting the sensor.

9. The sensor of claim 1, wherein said membrane is supported by a barrier having at least one hole.

10. The sensor of claim 9, wherein said barrier is made of silicone nitride.

11. A method for detecting an analyte, said method comprising the steps of:
    assembling a sensor that includes:
       a top cap capable of receiving a first electrolyte;
       a bottom cap capable of receiving a second electrolyte; and
       a flexible boot capable of holding said top cap, said bottom cap and a membrane located between the first electrolyte and the second electrolyte; and
    inserting the first electrolyte within said top cap;
    inserting the second electrolyte within said bottom cap;
    applying a voltage to the first electrolyte, the membrane and the second electrolyte; and
    measuring an electrical characteristic of the membrane, wherein the measured electrical characteristic can indicate the presence of the analyte.

12. The method of claim 11, further comprising the step of initiating an alarm when the measured electrical characteristic of an at least one ion channel in the membrane indicates the presence of the analyte.

13. The method of claim 11, wherein said detected analyte can indicate the presence of a hazardous chemical.

14. The method of claim 11, wherein said detected analyte can indicate the presence of spoiled food.

15. The method of claim 11, wherein said sensor can be used in a pharmaceutical drug screening application.

16. The method of claim 11, further comprising the step of positioning said sensor within a base assembly that helps prevent vibration and electromagnetic noise from adversely affecting the sensor.

17. The method of claim 11, wherein said membrane is supported by a barrier having at least one hole.

18. A sensor, comprising:
    a top cover;
    a center chamber, fixably attached to said top cover, capable of receiving a first electrolyte; and
    a lower chamber, fixably attached to said center chamber, capable of receiving a second electrolyte, wherein a membrane located between the first electrolyte and the second electrolyte is used to enable detection of an analyte;
    an electrical device, coupled to the first electrode and the second electrode, including:
       a voltage source for applying a voltage to the first electrolyte, the membrane and the second electrolyte; and
       a detector for measuring an electrical characteristic of the membrane; and
    said electrical device is further capable of initiating an alarm when the measured electrical characteristic of an at least one ion channel in the membrane indicates the presence of the analyte.

19. The sensor of claim 18, further comprising:
    a first O ring, associated with said center chamber, capable of retaining the first electrolyte; and
    a second O ring, associated with said lower chamber, capable of retaining the second electrolyte, wherein said membrane is located between said first O ring and said second O ring.

20. The sensor of claim 18, further comprising:

a first electrode, associated with said center chamber, capable of being in electrical communication with the first electrolyte; and a second electrode, associated with said lower chamber, capable of being in electrical communication with the second electrolyte.

21. The sensor of claim 18, wherein said top cover and said center chamber are fixably attached to one another using a hinge or a snap fit.

22. The sensor of claim 18, wherein said center chamber and said lower chamber are fixable attached to one another using a snap fit.

23. A method for detecting an analyte, said method comprising the steps of:

assembling a sensor that includes:
  a top cover;
  a center chamber, fixably attached to said top cover, capable of receiving a first electrolyte;
  a lower chamber, fixably attached to said center chamber, capable of receiving a second electrolyte; and
  a membrane located between the first electrolyte and the second electrolyte; and inserting the first electrolyte within said center chamber;

inserting the second electrolyte within said lower chamber;

applying a voltage to the first electrolyte, the membrane and the second electrolyte; and measuring an electrical characteristic of the membrane, wherein the measured electrical characteristic can indicate the presence of the analyte.

24. The method of claim 23, further comprising the step of initiating an alarm when the measured electrical characteristic of an at least one ion channel in the membrane indicates the presence of the analyte.

* * * * *